US012357829B2

(12) United States Patent
Allott

(10) Patent No.: US 12,357,829 B2
(45) Date of Patent: *Jul. 15, 2025

(54) SYSTEM AND RELATED METHOD FOR POSITIONING OF SURGICALLY IMPLANTED NEURO STIMULATION DEVICE ELECTRODES

(71) Applicant: THRESHOLD NEURODIAGNOSTICS LLC, Minoa, NY (US)

(72) Inventor: Geoffrey L. Allott, Minoa, NY (US)

(73) Assignee: THRESHOLD NEURODIAGNOSTICS LLC, Reedsburg, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/511,644

(22) Filed: Nov. 16, 2023

(65) Prior Publication Data

US 2024/0082581 A1 Mar. 14, 2024

Related U.S. Application Data

(63) Continuation of application No. 16/949,257, filed on Oct. 22, 2020, now Pat. No. 11,904,169.
(Continued)

(51) Int. Cl.
*A61N 1/36* (2006.01)
*A61N 1/05* (2006.01)
*A61N 1/372* (2006.01)

(52) U.S. Cl.
CPC ....... *A61N 1/36128* (2013.01); *A61N 1/0553* (2013.01); *A61N 1/36062* (2017.08); *A61N 1/37223* (2013.01); *A61N 1/0534* (2013.01)

(58) Field of Classification Search
CPC .......................... A61N 1/0551; A61N 1/0553
See application file for complete search history.

(56) References Cited

U.S. PATENT DOCUMENTS 5,983,141 A 11/1999 Sluijter et al.
7,177,690 B2 2/2007 Woods et al.
(Continued)

OTHER PUBLICATIONS

Allott et al., "Multimodal Spinal Cord Mapping during Spinal Cord Stimulator Placement: Technical Note," The Neurodiagnostic Journal, vol. 61, No. 4, p. 203-213, (2021).
(Continued)

*Primary Examiner* — Alyssa M Alter
(74) *Attorney, Agent, or Firm* — Hoxie & Associates LLC

(57) ABSTRACT

A system is provided for connecting a surgically implantable neurostimulation device to an neurophysiological monitoring device. The system includes an apparatus connecting the neurophysiological monitoring device to the implanted neurostimulation device. The connecting apparatus includes a port couplable to the neurostimulation device and a plurality of electrode pin connectors extending from the port that are connectable to the neurophysiologic monitoring device. Using the connecting apparatus, signals from the neurophysiologic monitoring device can be transmitted for stimulation and responses can be transmitted to the neurophysiologic monitoring device to enable accurate positioning of electrodes of the neurostimulation device.

8 Claims, 14 Drawing Sheets

Related U.S. Application Data

(60) Provisional application No. 62/927,191, filed on Oct. 29, 2019.

(56) References Cited

U.S. PATENT DOCUMENTS

| | | | |
|---|---|---|---|
| 7,536,266 | B2 | 5/2009 | Williams et al. |
| 11,904,169 | B2 * | 2/2024 | Allott ..................... A61B 5/407 |
| 2003/0199948 | A1 * | 10/2003 | Kokones .............. A61N 1/0551 |
| | | | 607/117 |
| 2004/0015211 | A1 | 1/2004 | Nurmikko et al. |
| 2006/0089697 | A1 | 4/2006 | Cross, Jr. et al. |
| 2006/0287678 | A1 | 12/2006 | Shafer et al. |
| 2012/0209346 | A1 | 8/2012 | Bikson et al. |
| 2019/0232062 | A1 * | 8/2019 | Falowski ............... A61B 5/395 |

OTHER PUBLICATIONS

Choi et al., "Multimodal, Intraoperative Monitoring during Paddle Lead Placement for Cervicothoracic Spinal Cord Stimulation," Stereotact Funct Neurosurg., vol. 93, No. 4, p. 271-281, (2015); Abstract only.

Falowski et al., "Analysis of S1 DRG Programming to Determine Location of the DRG and Ideal Anatomic Positioning of the Electrode," Neuromodulation, vol. 23, No. 2, p. 252-257, (2020), ePub 2019; Abstract only.

Falowski et al., "Multicenter Retrospective Analysis of Dorsal Root Ganglion Stimulator Placement Using Intraoperative Neuromonitoring in Asleep Patients During Early Period of Adoption," Neuromodulation: Technology at the Neural Interface, vol. 24, No. 4, p. 753-757, (2021).

Falowski et al., "Nonawake vs Awake Placement of Spinal Cord Stimulators: A Prospective, Multicenter Study Comparing Safety and Efficacy," Neurosurgery, vol. 84, No. 1, p. 198-205, (2019); Abstract only.

Mammis et al., "The Use of Intraoperative Electrophysiology for the Placement of Spinal Cord Stimulator Paddle Leads Under General Anesthesia," Neurosurgery, vol. 70, No. 2 Suppl Operative, p. 230-236, (2012); Abstract only.

Nair et al., "Dorsal Column Mapping via Phase Reversal Method: The Refined Technique and Clinical Applications," Neurosurgery, vol. 74, No. 4, p. 437-446, (2014).

Shils et al., "Neuromonitoring for Spinal Cord Stimulation Lead Placement Under General Anesthesia," J Clin Neurol, vol. 14, No. 4, p. 444-453, (2018).

Yingling et al., "Use of Antidromic Evoked Potentials in Placement of Dorsal Cord Disc Electrodes," Appl Neurophysiol., vol. 49, No. 1-2, p. 36-41, (1986); Abstract only.

* cited by examiner

SYSTEM AND RELATED METHOD FOR POSITIONING OF SURGICALLY IMPLANTED NEURO STIMULATION DEVICE ELECTRODES

CROSS REFERENCE TO RELATED APPLICATIONS

This present application is a continuation of U.S. patent application Ser. No. 16/949,257, filed on Oct. 22, 2020, which claims the benefit of provisional patent application Ser. No. 62/927,191 filed 2019 Oct. 29 by the present inventor, which are incorporated by reference in their entireties.

TECHNICAL FIELD

This application generally relates to the field of neuromodulation, and more particularly, to a system, apparatus and related method that enables the interconnection of a surgically implanted neuromodulating device with at least one neurophysiologic monitoring device in order to enable accurate positioning of the electrodes of the implanted neuromodulating device.

BACKGROUND

Neural modulation (or neuromodulation) has been proposed as a therapy for a number of patient-related conditions. Neural modulation and neural stimulation (or neurostimulation) are terms often used interchangeably or synonymously in order to describe excitatory stimulation that causes action potentials, as well as inhibitory and other effects. Examples of neuromodulation-based processes include Spinal Cord Stimulation (SCS), Deep Brain Stimulation (DBS), Peripheral Nerve Stimulation (PNS), and Functional Electrical Stimulation (FES).

Targeted neuromodulation therapies generally offer a treatment option that is non-opiate based, has minimal side effects, is relatively safe and potentially reversible. In this regard, some neural targets may be complex structures with different types of nerve fibers. An example of such a complex structure is the neuronal elements in and around the spinal cord that are targeted by SCS.

SCS, by way of example, has been particularly effective as an adjunct in the treatment of mixed neuropathic/nociceptive and neuropathic/radicular pain conditions that is not amenable to conservative therapy, such as failed back syndrome (FBSS) and complex regional pain syndrome (CRPS). This form of targeted neuromodulation therapy, first used on patients in 1967, has since been routinely used to treat chronic pain syndromes by electrical stimulation of the dorsal columns.

In traditional SCS therapies, the principle is to replace the pain sensation with paresthesia that requires the mapping of stimulation to the region of pain in the spinal column. Typically, a low frequency dose of electrical current is applied by a connected pulse generator to a surgically implanted SCS electrode, which alters pain processing by masking the sensation of pain with a comfortable tingling or paresthesia. While paresthesia-based SCS therapies now represent the traditional approach to neuromodulation of various chronic pain syndromes, other novel SCS-based paradigms such as Dorsal Root Ganglion stimulation (DRG-S), paresthesia-free (SCS) paradigms, Burst SCS (B-SCS), High-Frequency (HF-SCS) and Evoked Compound Action Potential SCS (ECAP-SCS), among others, have also been developed and the field is ever evolving.

SCS stimulation is provided through electrodes that are percutaneously placed within the epidural space or more preferably through a surgically implantable paddle lead that is delivered via a laminotomy. A typical neurostimulation device is a surgically implantable SCS paddle lead defined by an relatively thin elongate member made from silicone or other biologically inert material. The paddle lead includes a plurality of electrical contacts in a formed array, typically having between 2 and 32 contacts. The number of contacts of the SCS paddle lead can be varied depending on the manufacturer.

An implantable pulse generator is coupled to the paddle lead following surgical implantation and mapping of the spinal cord to insure correct positioning of the electrode. These implanted SCS devices are capable of delivering pulse frequencies in the range of 2-1000 Hertz, but are regularly utilized at about 40-60 Hertz.

As noted, devices for neural modulation are commonly surgically implanted. However and due to physiological differences among patients, neural modulation may be unsuccessful at delivering inhibitory and other desired effects. One specific cause of failure is the mis-positioning of the stimulator electrode(s) relative to idiosyncratic patient physiology. Surgical revision rates due to mis-positioning of SCS electrodes in patients are reported to be as high as 30.1% of all cases.

A common technique used historically for the placement of SCS electrodes requires direct interaction with the patient with the SCS leads being initially and percutaneously implanted within the spinal cavity and with the wires of the implanted electrode connected to an external pulse stimulator unit. Direct interaction with the patient is required to awaken the patient during surgery in order to respond to sensations generated by stimulation for the purposes of properly positioning the leads on the spinal column of the patient with the incisions open and anesthetized. During that intraoperative wake up time, the patient is questioned by the surgical team to insure the stimulation is perceived in the correct region of their body. Once this is established, the wires are connected to the percutaneously implanted pulse generator of the SCS stimulation device.

The sensations perceived and related by the patient during surgery for positioning of the SCS electrodes have been demonstrated to be unreliable or misleading for a number of reasons. Among these reasons are the patient's inability to discern their pain syndrome from the effects of surgery or the feeling of stimulation at the time of testing.

Intraoperative neurophysiological monitoring (IONM) or intraoperative neuromonitoring is another discipline that generally consists of stimulating neural tissue and analyzing responses (generally in the form of electrical waveforms) generated by the stimulus. More specifically, IONM is the use of electrophysical methods such as electroencephlaography (EEG), electromyography (EMG), and evoked potentials to monitor functional integrity of certain neural structures (e.g., the nerves, spinal cord and parts of the brain) during surgery and reduce the risk of damage to the nervous system and provide functional guidance to the surgeon and anesthesiologist.

For a given surgery, the set of modalities used depends in part on which neural structures are at risk. During surgery, a trained neurophysiologist attaches a computer system to the patient using stimulating and recording electrodes. Interactive software running on the IONM system then selectively activates the stimulating electrodes with appropriate timing wherein the electrophysiologic signals picked up by the recording electrodes are processed and displayed. The resulting signals change according to various factors wherein the surgeon, anesthesiologist, and neurophysiologist differentiate signal changes over time in light of the various factors.

The prior art, particularly that of Shilles and Arle as discussed in their paper, *Neuromonitoring For Spinal Cord Stimulation Lead Placement Under General Anesthesia*, contemplate the use of implantable SCS devices in conjunction with IONM equipment for determining or verifying correct SCS paddle placement. Specifically, Shilles and Arle describe the stimulation of SCS paddles placed on the dura and receipt of that stimulation information by IONM equipment. As described, this is achieved by using an SCS paddle stimulation device that allows stimulation at supra-therapeutic ranges in order to overcome the sedative effects of anesthesia. This stimulation is received by the IONM equipment for interpretation in order to determine whether the SCS paddle is correctly placed in the patient while under sedation.

Overall, there is still a pervasive and general need in the field to reduce the rate of improper or incorrect placement of surgically implantable neuromodulation devices, such as SCS paddles. There is also a compelling need to be able, if needed, to utilize different mapping techniques contemporaneously for an SCS or other surgically implantable neuromodulating device using connected neurophysiological or other monitoring equipment.

BRIEF DESCRIPTION

It is therefore one object of the present invention to be able to interconnect neuromodulation and intraoperative neurophysiological monitoring devices in a unique and novel manner that offers a means to overcome patient physiological differences, as well as reduce neuromodulation device failure rates due to errors in positioning the devices.

Therefore and according to one aspect of the present invention, there is provided a system for connecting a surgically implanted neurostimulation device to a neurophysiologic monitoring device for purposes of accurately positioning the electrodes of the neurostimulation device. The system comprises an apparatus enabling stimulation signals to be transmitted from the neurophysiologic monitoring device to the neurostimulation device, in which the apparatus further enables recording signals to be received by the neurophysiological monitoring device through a common interconnection.

More specifically and according to a preferred embodiment, a wire harness interconnects the neurostimulation device and the neurophysiological monitoring device, the wire harness having a connector port attachable to the neurostimulation device and a plurality of electrode pin connectors for connection to the neurophysiological monitoring device(s). According to a preferred embodiment, the electrode pin connectors are DIN pin connectors. As such, stimulation and recording can be accomplished for purposes of positioning the surgically implanted neurostimulation device using a common interconnection.

According to one embodiment, the neurostimulation device is an SCS stimulation device, such as an SCS paddle lead having a plurality of electrical contacts that is surgically implanted within the patient and the neurophysiological monitoring device is an intraoperative neurophysiological monitoring (IONM) device, each commonly attached to the wire harness. According to another embodiment, the neurostimulation device is one of the group consisting of Spinal Cord Stimulation (SCS), Deep Brain Stimulation (DBS), Peripheral Nerve Stimulation (PNS), and Functional Electrical Stimulation (FES) devices.

According to yet another aspect of the present invention, there is provided a method for connecting a surgically implanted neurostimulation device to a neurophysiologic monitoring device for mapping of electrodes of the neurostimulation device, the method comprising: connecting the surgically implanted neurostimulation device to a connecting apparatus; connecting leads of the connecting apparatus to the neurophysiological monitoring device; and transmitting at least one stimulation signal using the neurophysiological monitoring device via the connecting apparatus and obtaining at least one recording signal at the neurophysiological monitoring device from the neurostimulation device based on the at least one stimulation signal for purposes of accurately positioning the neurostimulation device.

According to another aspect of the present invention, there is provided an apparatus configured for use with a surgically implantable neurostimulation device for positioning of the device, said apparatus comprising:
  a wire harness comprising:
    a port configured for attachment to the neurostimulation device;
    a hub at the proximal end of the harness; and
    a plurality of electrode pin connectors extending from the hub, the plurality of electrode pin connectors adapted for connection to a neurophysiologic monitoring device.

The present invention presents a novel system, apparatus and related method that enables both stimulation of a neurostimulation device, such as a surgically implanted SCS paddle, and receipt of monitoring recording signals by the neurophysiological monitoring equipment (an IONM device) for purposes of mapping/locating the electrodes of the neurostimulation device. This invention presents a significant advancement over the prior art in several ways and offers a number of advantages in use.

First, stimulating the neurostimulation or neuromodulation device directly from a mutually connected neurophysiological (e.g., IONM) device eliminates the risk of uncoordinated stimulation between the neurostimulation device and the IONM device, as the neurostimulation device and the IONM device are different and unique apparatus. Specifically and as different devices, the stimulation and receipt of the stimulation is performed by different devices from different vendors opening the opportunity for uncoordinated signal(s) and receipt. Commonly, an SCS paddle or other neurostimulation device is operated by the surgeon on the surgical field; whereas, the IONM device is out of the sterile field.

Second, stimulation signals originating from the IONM device/equipment enables a far wider and greater range of sub and supra therapeutic stimulation ranges, frequencies, and voltages. This facilitates the mapping and placement of the electrodes of the neural stimulation device(s) in difficult, complex and non-standard cases.

Third, the herein described apparatus also enables synchronized cortical and peripheral recordings to stimulation so that various mapping techniques can be run concurrently during SCS paddle or other implantable neuromodulating device placement. This provides a significant improvement over the prior art where only a single mapping technique can be conducted at the same time.

Fourth and in addition, the herein described device and method also allow for recording directly from the spinal cord in response to either cortical or peripheral stimulation. This bidirectional ability allows users of the herein described system to access literally all known spinal cord mapping techniques.

Furthermore, stimulation from the IONM device simplifies operation to a single IONM device entirely off of the surgical field. This simplifies the procedure to only minutes, thereby reducing the overall surgical time including the duration of sedation.

In addition, stimulation is controlled by a single person. As a result, miscommunication and/or errors of the conceptual application of stimulation signals are avoided.

Using the herein described system and method, the precise parameters of stimulation are automatically recorded by the neurophysiological monitoring equipment including pulse duration, frequency, repetition rate and number of trials. Moreover, exact quantitative recordings from the patient can be stored quickly and easily.

With regard to spinal cord stimulation (SCS) in particular, the herein described system and apparatus builds skills in spinal cord mapping that cannot be otherwise obtained and are applicable to very difficult case situations, including those that do not necessarily involve connections to an impaired SCS electrode. For example, cases such as intermedullary spinal cord tumors require the same mapping techniques can derive benefit.

These and other features and advantages will be readily apparent from the following Detailed Description, which should be read in conjunction with the accompanying drawings.

BRIEF DESCRIPTION OF THE DRAWINGS

FIG. 3(a) is an enlarged view of a screening cable of FIG. 3;

DETAILED DESCRIPTION

Figure 1:
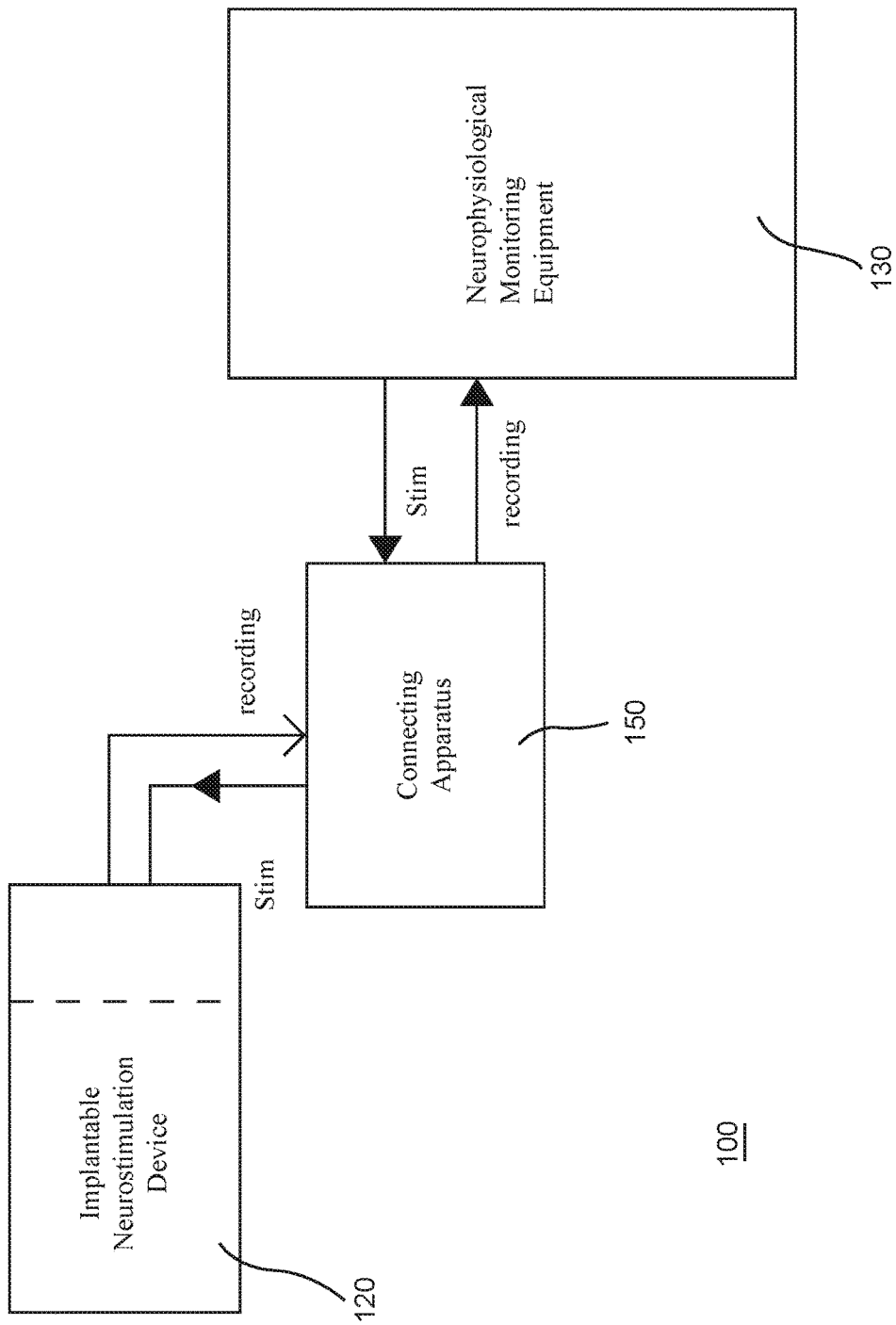
FIG. 1 illustrates a schematic block diagram of a generic system in accordance with various aspects of the present invention.

The following Description relates to a system and apparatus for interconnecting a surgically implantable neurostimulation device and neurophysiologic monitoring equipment (e.g., an IONM system), for purposes of accurately positioning the electrodes of the implanted neurostimulation device, as well as a related method. The specific Description that follows is an exemplary embodiment directed to a specific surgically implantable neurostimulation device; namely, a spinal cord stimulation (SCS) paddle lead. It will be understood, however, that the various concepts described herein can be used for literally any surgically implantable neurostimulation device, including but not limited to Deep Brain Stimulation (DBS), Peripheral Nerve Stimulation (PNS) and Functional Electrical Stimulation (FES) devices.

Throughout this Description, various terms are used in order to provide a suitable frame of reference for the accompanying drawings. These terms, which include "distal", "proximal", "above", "below", "beneath", "interior", 'exterior", "inner", "outer", and the like are not intended to be over limiting of the herein described system or components thereof or the inventive method of using the system and system components, except where so clearly and specifically indicated.

In addition, the accompanying drawings are also intended to illustrate the salient features of the herein described invention. Accordingly, the drawings are not to scale and should not be used for scaling purposes. Reference numerals are used throughout to identify components and features of the present invention in accordance with a number of embodiments. In some instances, the same reference numerals will be used to identify similar components, for the sake of clarity.

A block diagram is provided at FIG. 1, which generically depicts a positioning system in accordance with aspects of the present invention. This system, herein labeled with the reference numeral 100, includes a surgically implantable neurostimulation device 120, as well as a neurophysiologic monitoring device 130, each shown diagrammatically. Each of the devices 120, 130 are interconnected via an intermediately disposed connecting apparatus 150. As depicted and further described herein, the connecting apparatus 150 is configured for coupling to the neurostimulation device 120 as well as the neurophysiological monitoring device/equipment 130. Details relating to each of the components of the system 100 are further discussed in this application.

Figure 2:
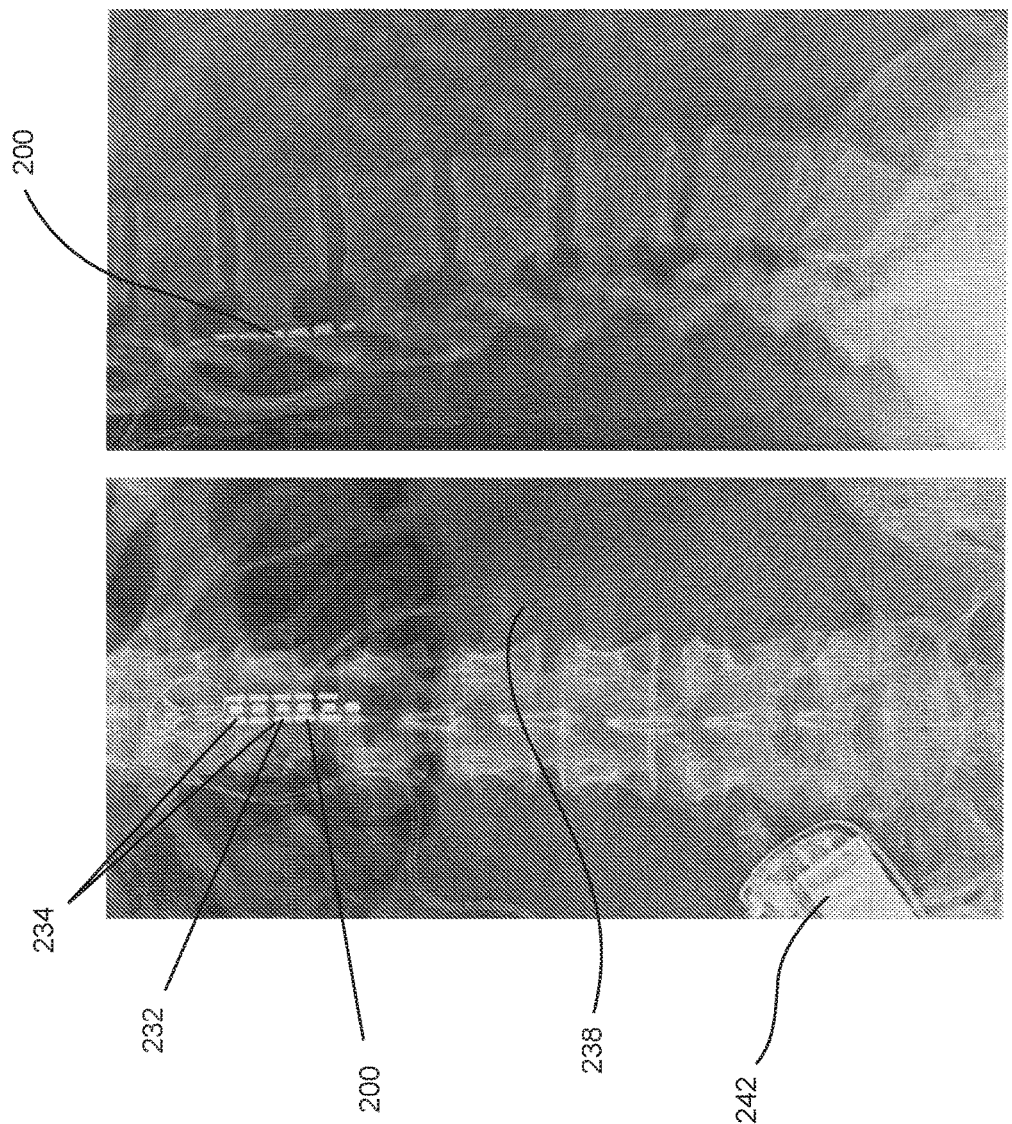
FIG. 2 illustrates an exemplary neuromodulating or neurostimulation device, the device being surgically implanted within a patient.

As noted and for description purposes only, the following is directed to a specific form of neuromodulating device 200; namely an SCS stimulation device which is implanted surgically within the spinal column of a patient, as depicted in FIG. 2. This neurostimulation device 200 is an SCS paddle lead 232, preferably having a plurality of electrical contacts 234. As discussed herein, the number of electrical contacts 234 can be varied. A series of wire leads 238 extend from the proximal end of the implanted paddle lead 232 to a pulse generator 242 that is also surgically implanted within the patient. The pulse generator 242 is battery operated and configured to transmit electrical stimulation signals through the wire leads 238 to the electrical contacts 234 of the paddle lead 232 via a wireless (RF) remote control (not shown) that is maintained by the patient.

Figure 3:
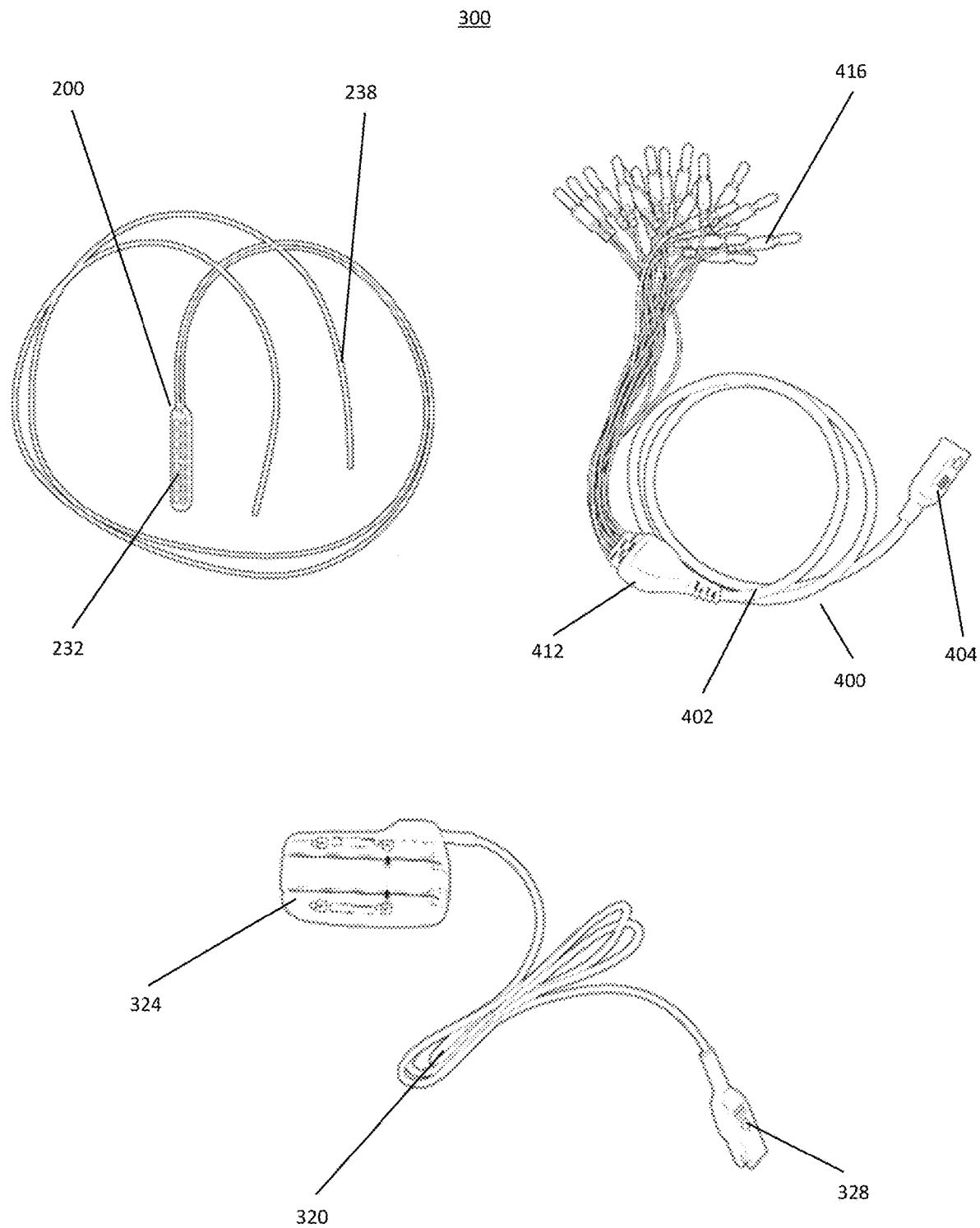
FIG. 3 is a partial assembly view of components of an exemplary system and in accordance with various aspects of the present invention.
Figure 3:
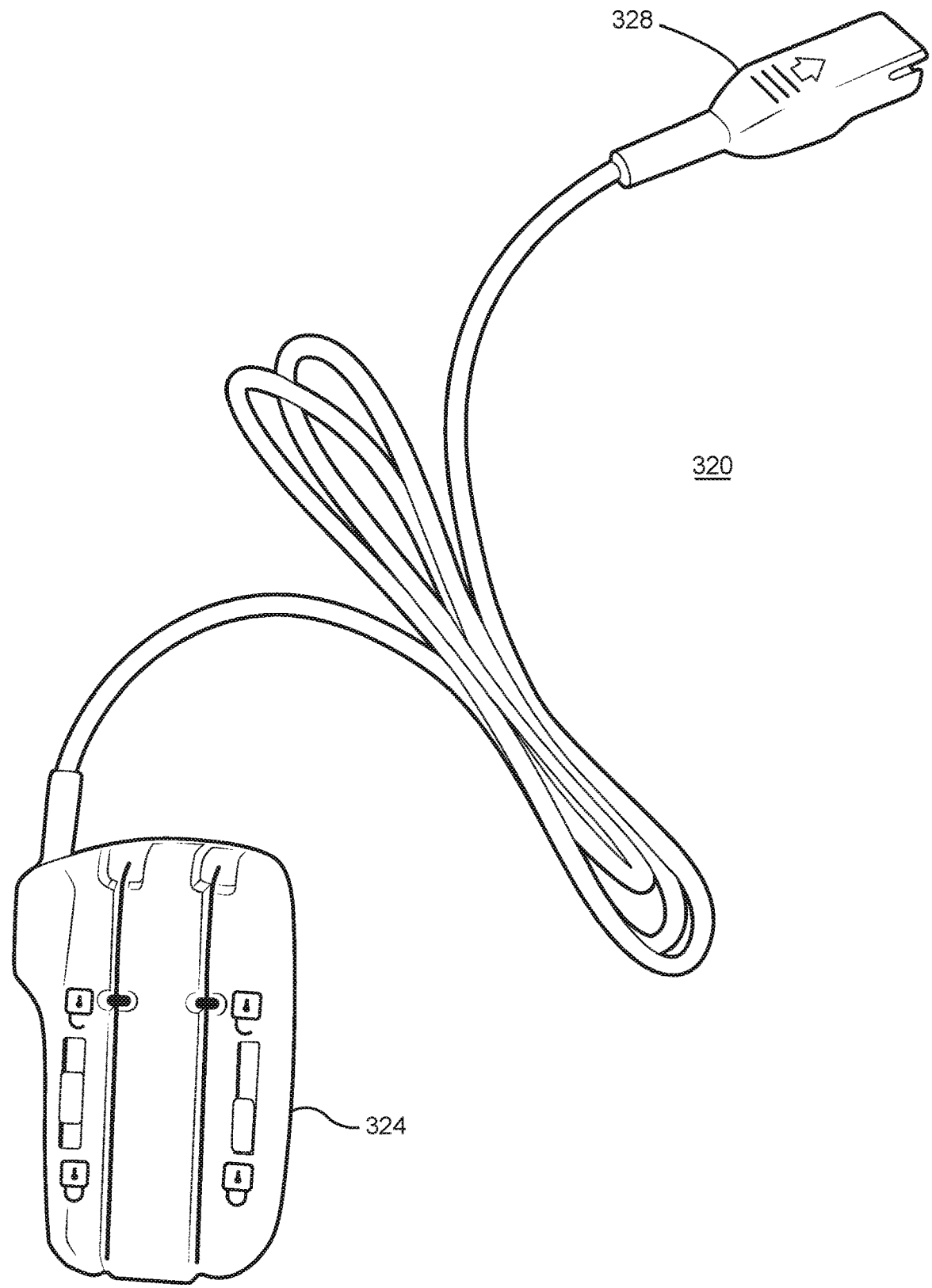

FIG. 3 depicts a partial assembly view of various components of an exemplary system 300 in accordance with the present invention. The system 300 includes a neuromodulation device 200, which in this example is a SCS paddle lead 232 similar to that previously illustrated in FIG. 2, as well as an intermediately disposed connecting apparatus 400. As previously described, the SCS paddle lead 232 is surgically implanted within a patient and includes a plurality of electrical contacts 234. A set of wire leads 238 extending from the proximal end of the SCS paddle lead 232 are connectable to a screener cable 320 having a distal portion 324 that retains the extending wire leads 238 of the implantable SCS paddle lead 232 and a pinned connector port 328 at its proximal end of the cable 320, the latter being further shown in FIG. 3(a). The screener cable 320 is typically provided by the manufacturer or vendor of the SCS paddle lead 232.

Figure 4:
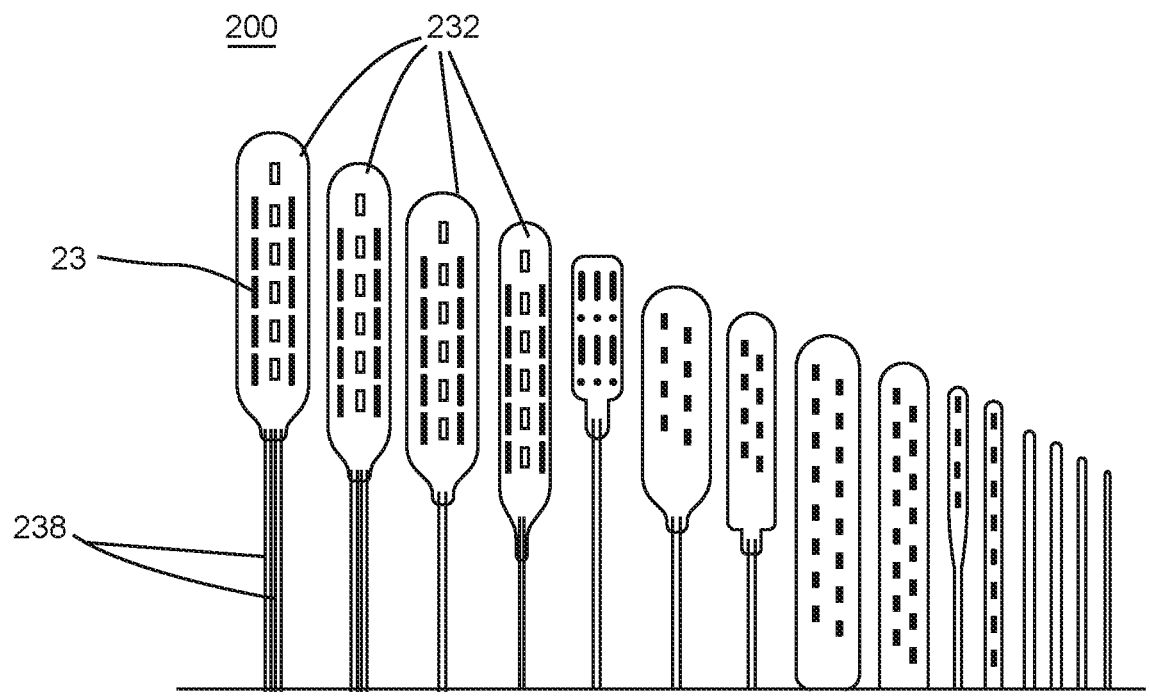
FIG. 4(a) is a plan view of various neuromodulating devices that can be alternatively be used with the systems of FIGS. 1 and 3.
FIG. 4(b) is a partial perspective view of one of the neuromodulating devices shown in FIG. 4(a)
FIG. 4(c) is an enlarged schematic view of the electrode of the neuromodulating device of FIG. 4(b), including a numbering sequence of the electrical contacts.
FIG. 4(d) is a partial view of another exemplary neuromodulating device and more specifically the implantable electrode stimulation device.
FIG. 4(e) is a perspective view of the neuromodulating device of FIG. 4(d)
Figure 4:
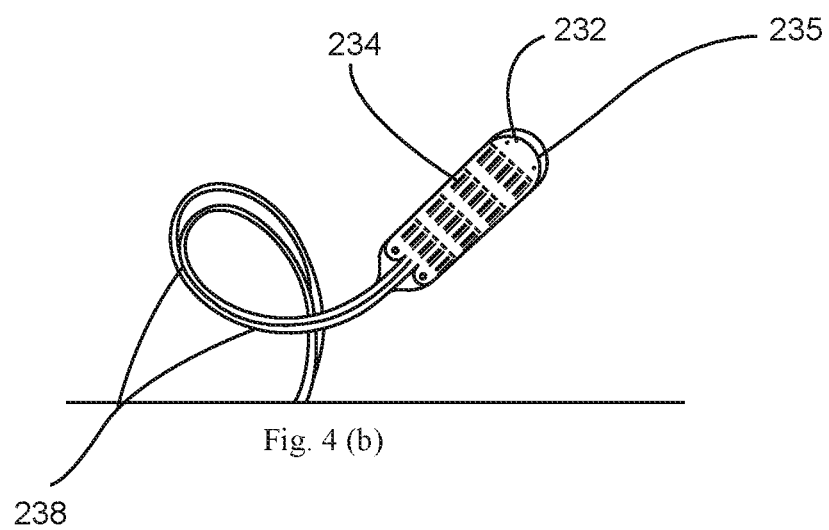
Figure 4:
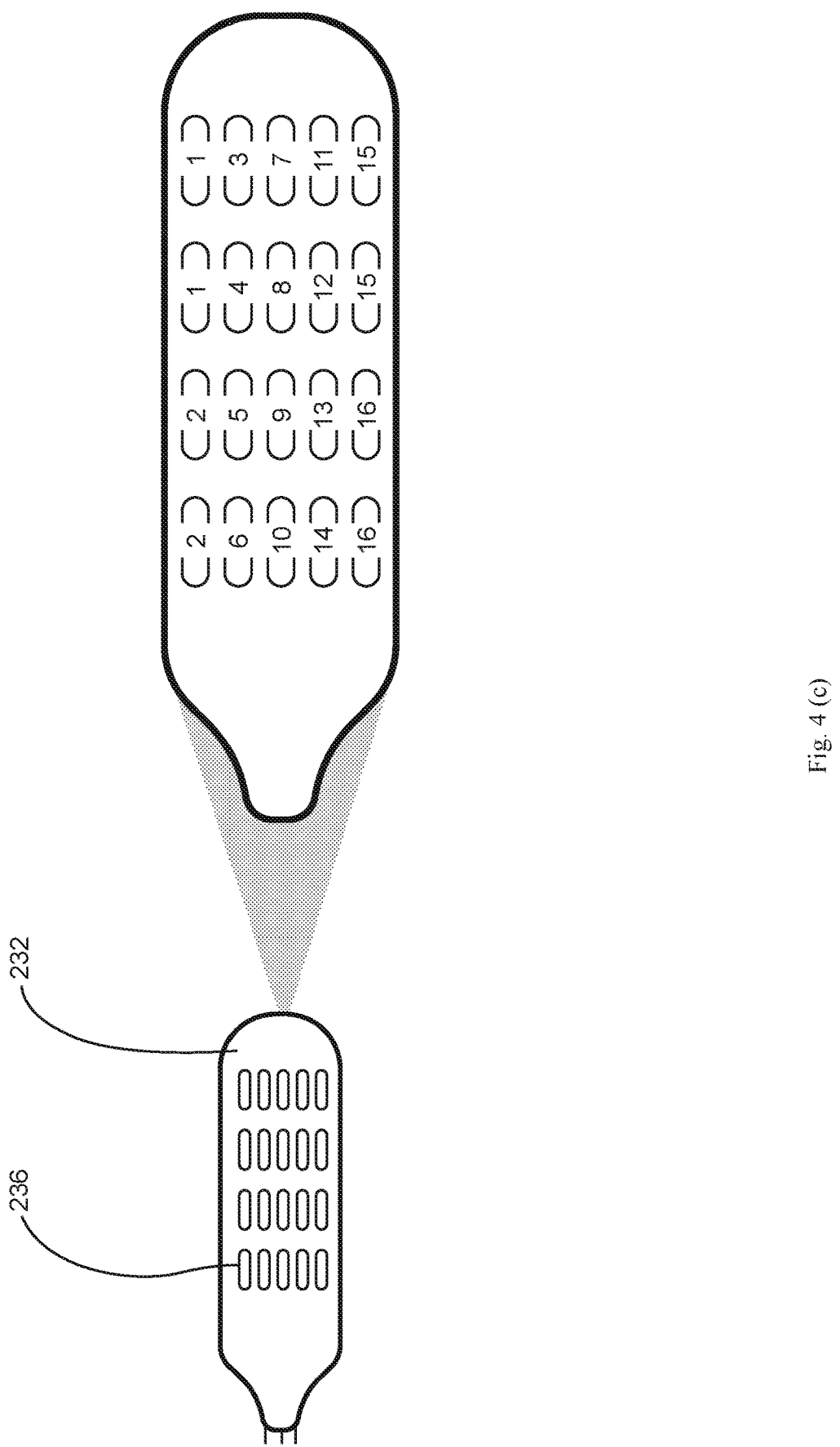

The form of the SCS paddle can include one of many designs. FIG. 4(a) illustrates designs of various implantable SCS paddle leads 232 that can be used in the exemplary system shown in FIG. 3. Each SCS paddle lead 232 commonly comprises an elongate member made from silicone or similar biologically inert material. SCS paddle leads are typically used in permanent spinal cord stimulation and are preferred over percutaneous leads in terms of their ability to provide long term stimulation for the patient. Percutaneous leads are round and thin and approximately 2 mm wide. Their electrical contacts are circumferential around the lead. This means that the electrical energy is dissipated 360 degrees around the lead that can disperse energy in nonessential directions and will waste energy in stimulating tissue unnecessarily for a desired pain treatment effect (spinal cord, nerve roots).

Conversely, the SCS paddle lead 232 is silastic coated and insulated on one side to prevent the discharge of current to tissue on that one side. This allows the energy to be uni-directional so that that energy is precisely focused on the target anatomy. In addition, SCS paddle leads 232 are more stable than percutaneous wire leads given the wider shape of the paddle and increased surface area, the latter providing a greater surface area for scar to form around it. The number of electrical contacts 234 of the SCS paddle lead 232 can be varied depending on the manufacturer and typically include 2-32 contacts, or more. This reduces the chances of electrode migration following the implantation procedure.

The SCS paddle leads 232 depicted in FIG. 4(a) are manufactured and sold by St. Jude Medical, Inc (a division of Abbott Laboratories). However, there are a number of other vendor/manufacturers of these devices including Medtronic, Boston Scientific Corporation, and Nuvectra Corporation, among others. As noted previously, the inventive system, connecting apparatus and method are intended for use with any surgically implantable SCS devices, as well as other neurostimulation/neuromodulating devices.

FIGS. 4(b) and 4(c) partially illustrate one of the SCS paddle leads 232 shown in FIG. 4(a). According to this embodiment, the SCS device is a Penta Paddle Lead, manufactured and sold by St. Jude Medical, Inc. As more clearly shown in FIGS. 4(b) and 4(c), the Penta implantable SCS paddle electrode 235 includes 5 columns, each column having four (4) electrical contacts 234 for a total of (20) twenty electrical contacts. As shown in FIG. 4(c) and in terms of designation, the first column of the SCS paddle lead 232 is sequenced reading down with the following contact designations: 1, 1, 2, 2. The second column is sequenced with the following contact designations: 3, 4, 5, 6. The third column of the herein described SCS paddle lead 230 is sequenced with the following contact designations: 7, 8, 9, 10, the fourth column is sequenced: 11, 12, 13, 14 and the fifth column of the SCS paddle lead 230 is sequenced with the following contact designations: 15, 15, 16, 16. Each of the electrical contacts 234 are connected to a wire lead 238 extending proximally from the paddle head 235.

Figure 4D:
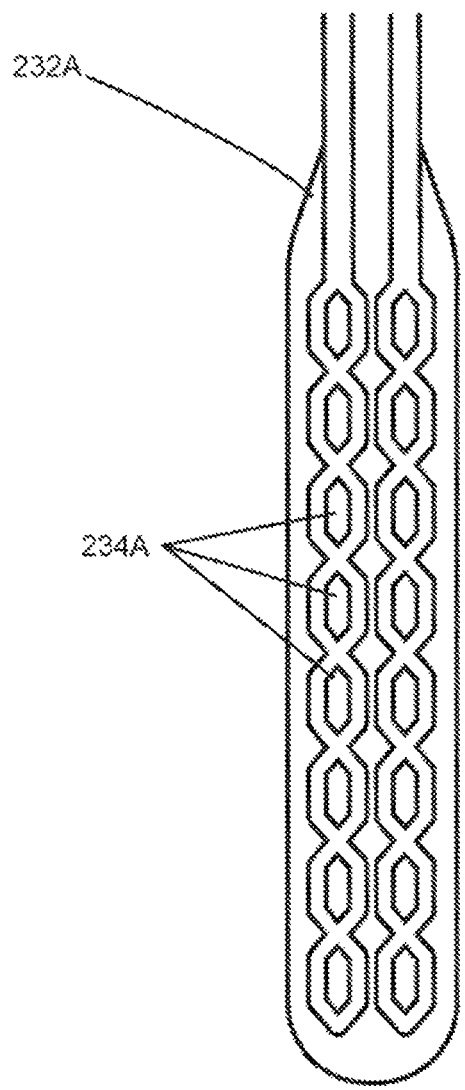
Figure 4:
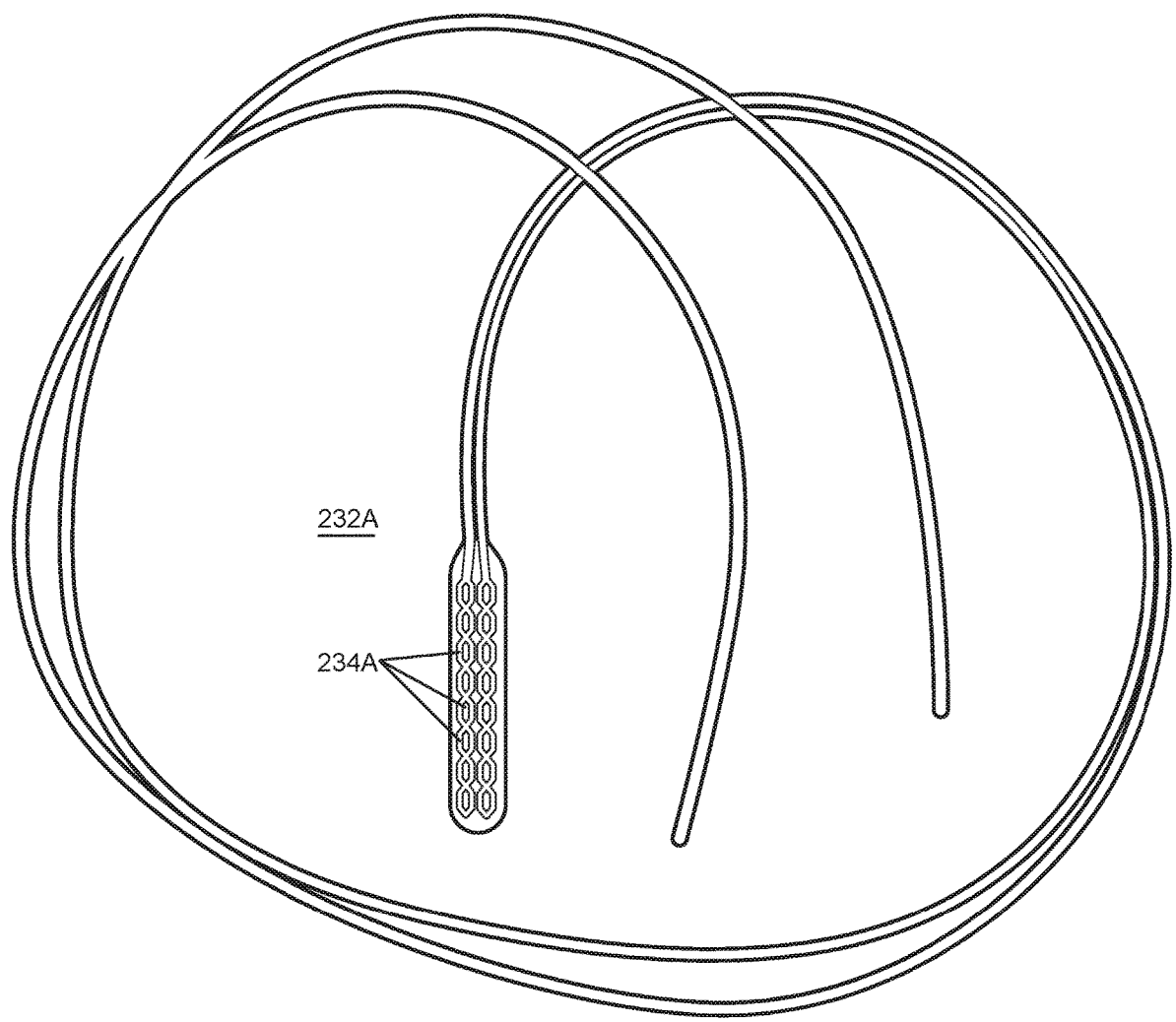
Figure 5:
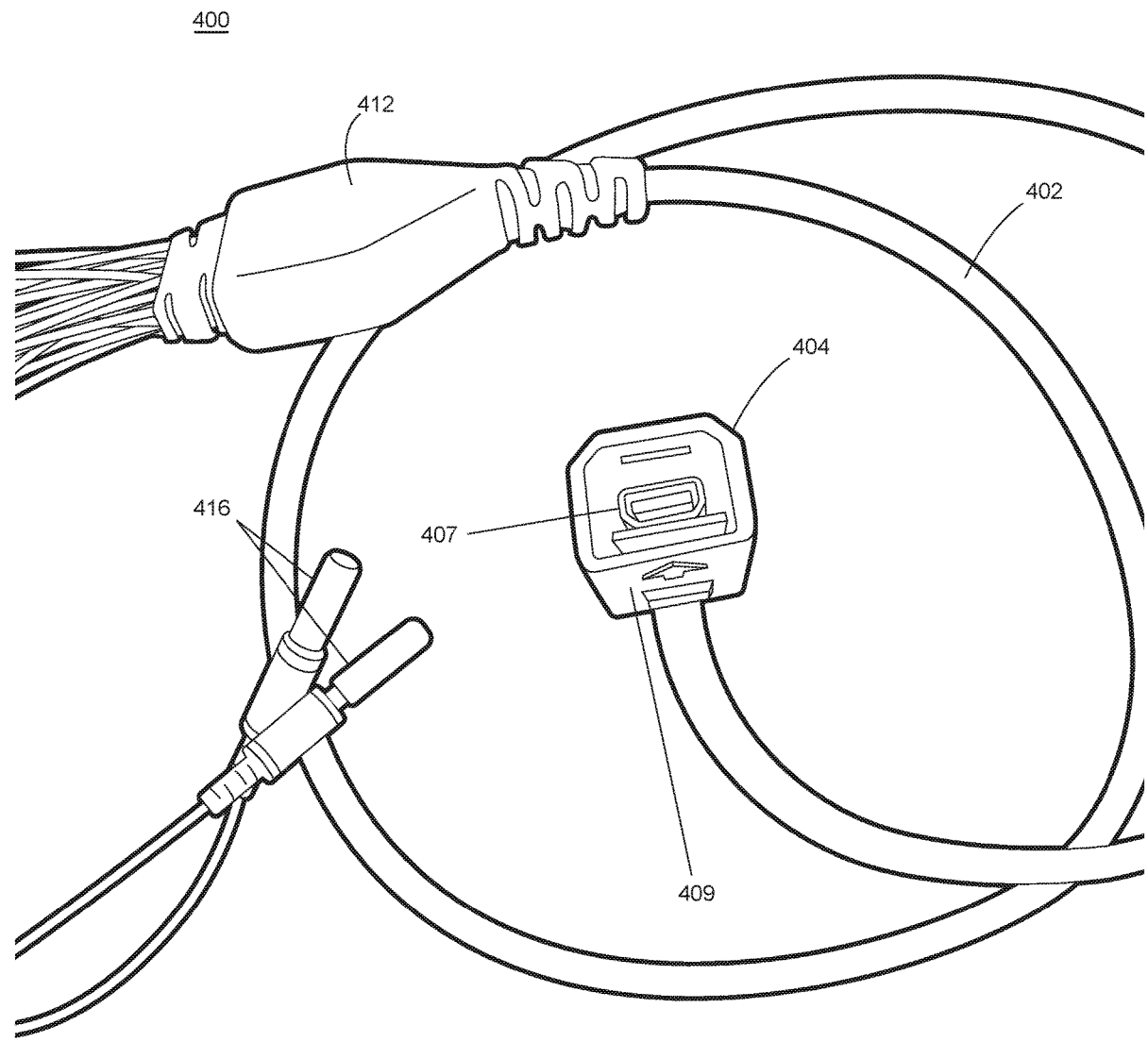
FIG. 5(a) is an enlarged view of the connector apparatus shown in FIG. 3.
FIG. 5(b) is a perspective view of the connector apparatus of FIGS. 3 and 5(a)
Figure 5:
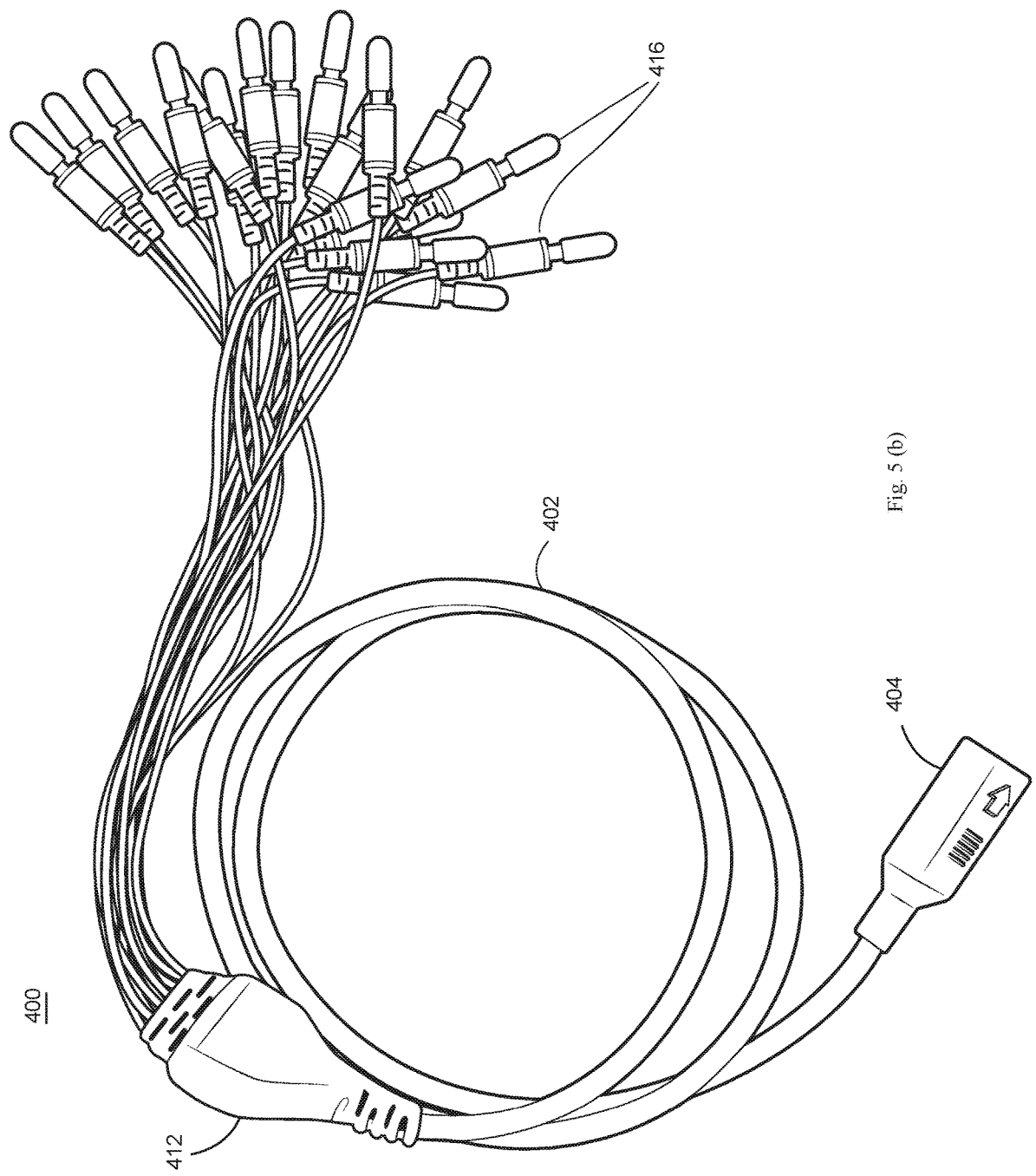

A similar SCS paddle electrode or lead 232A, manufactured by Boston Scientific, is shown in FIGS. 4(d) and 4(e), this electrode 232A having a plurality of electrical contacts 234A according to a different 2×8 electrical contact configuration.

With reference to FIGS. 3, 5(a), 5(b) and 6, the connecting apparatus 400 according to this embodiment is defined by an insulated cable 402 having a connector port 404 at its distal end and a plurality of electrode pin connectors 416 individually extending from a hub 412 provided at the proximal end of the insulated cable 402. More specifically and according to this embodiment, the pin connectors 416 are 1.5 mm DIN connectors. The connector port 404 is sized and configured to receive the proximal end connector 328 of the screener cable 320. As more closely shown in FIG. 5, the connector port 404 is defined by an outer enclosure 409 and a center DIN connector 407 that is sized and configured to interconnect with the proximal end connector 328 of the screener cable 320. The hub 412 is disposed at the proximal end of the insulated cable 402 with the plurality of DIN pin connectors 416 extending individually from the hub 412.

Figure 6:
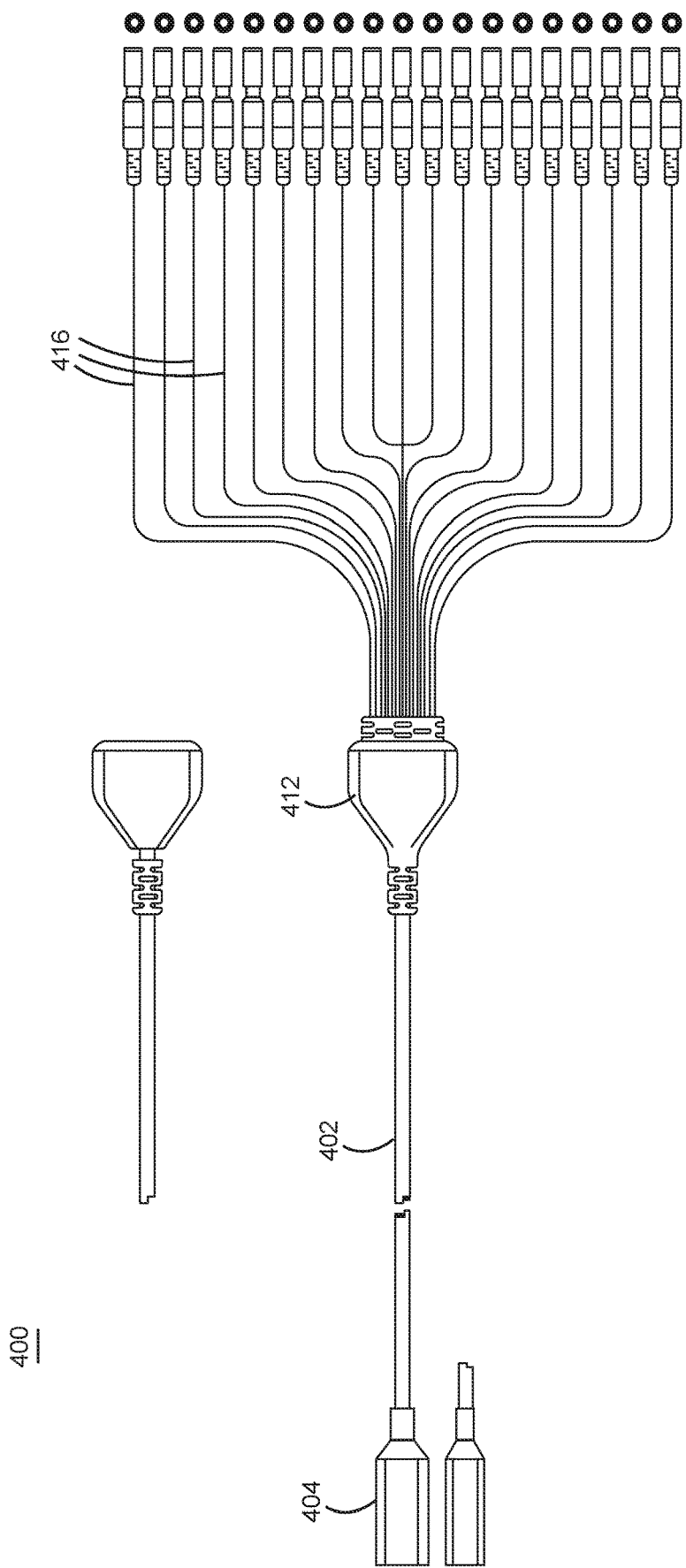
FIG. 6 is a wire schematic diagram of the connector apparatus of FIGS. 3 and 5.

As shown in FIG. 6, each of the DIN pin connectors 416 are numbered in order to correspond to the pins of the connector port 328 of the screener cable 328, and ultimately the electrical contacts 234 of the implanted SCS paddle lead 232. More specifically, the DIN pin connectors 416 are provided in a numbered sequence that approximates the order of connections of the implanted electrode. For example, the Medtronic 32 SCS paddle employs a 4×8 contact configuration with each of the columns being designated 1-8. Similarly, the Boston Scientific paddle 232A of FIGS. 4(d) and 4(e) employs a 2×8 configuration in which each of the columns are also designated 1-8. According to another example and when using the St. Jude Medical Penta SCS paddle electrode 232 depicted according to FIGS. 4(b) and 4(c), the numbering sequence is 1-16, meaning that the user must redefine or reassign the first electrical contact 1 in the second column, as 9 according to this latter numbering sequence.

Figure 7:
FIG. 7 is a flow chart briefly detailing an exemplary method of use in accordance with aspects of the present invention.

With reference to FIG. 7, a specific procedure or method using the herein described system 300, FIG. 3, is now described, with additional reference being made as needed to the components shown in FIGS. 2-6 for purposes of accurately positioning the electrodes of a surgically implanted SCS paddle lead and more specifically according to this embodiment, e.g., the St. Jude Medical Penta SCS paddle lead 232 of FIGS. 4(b) and 4(c) or the Boston Scientific paddle 232A of FIGS. 4(d) and 4(e).

First and according to a first step 502, the neuromodulating device is surgically implanted. In accordance with the exemplary system of FIG. 3, the SCS paddle lead 232 is surgically implanted into the spinal column of the patient via a laminotomy. Typically, this implantation is made into the posterior epidural space in which the paddle lead 230 is positioned on either side of the midline of the spinal column between T8-T10 for lower limb pain and between C4-C7 for upper limb pain. It will be understood that other suitable locations are within the purview of this described procedure.

Following this implantation and according to step 506, the neuromodulating device is attached to the connector apparatus 400. In the exemplary embodiment according to FIG. 3 and prior to this step, the screener cable 320 which as noted is typically provided by the manufacturer/vendor of the implantable paddle lead 232 is connected in a conventional manner to the SCS paddle lead 232. More specifically, the distal portion 324 of the vendor provided screener cable 320 is connected to the extending wire leads 238 of the paddle lead 232 with the various contacts 234 of the paddle lead 232 corresponding to male/female contacts where they connect to male/female contacts and are then converted to pins via a breakout board (not shown) that terminate in 1.5 mm DIN connectors provided in the pinned connector port 328 disposed at the proximal end of the screener cable 320.

The proximal end of the screener cable 300 is then removed from the sterile field and the pinned port 328 is attached by a technician to the connecting apparatus 400 of the present invention. More specifically, the connector plug 328 at the proximal end of the screener cable 320 is mated with the pinned connector port 404 at the distal end of the connector apparatus 400.

According to step 510, the neurophysiological monitoring equipment is then attached to the connecting apparatus. For the exemplary system of FIG. 3, the DIN electrode connecting pins 416 of the connecting apparatus 400, which are numbered in correspondence to the electrical contacts of the SCS paddle lead 232 are connected to a neurophysiological monitoring apparatus, such as an intraoperative neurophysiological monitoring (IONM) device 130, FIG. 1. Neurophysiological devices typically include electrical stimulators, differential amplifiers, frequency filters and software that resolves signals from interference, such as Fourier transformation and signal averaging.

According to this embodiment and prior to surgery, the contact assignments of the implanted paddle lead 232 are designated, such as by writing the contact assignments on paper. The DIN connector pins 416 are numbered to correspond with the electrical contacts 234 of the implantable SCS device 232. The electrical contacts are then selected for either recording or stimulation with the plurality of electrode connector pins 416 being plugged into the neurophysiological monitoring equipment 130, FIG. 1, (e.g., IONM device), as necessary.

Stimulation signals can then be transmitted to the neurophysiological modulating device using the neurophysiological monitoring equipment via the connecting apparatus 400 with recording signals being transmitted to the neurophysiological equipment based on the stimulating signals. Mapping can then be conducted according to step 518 and the electrode of the implanted device 232 can be positioned according to step 522.

Following mapping and in the exemplary embodiment of FIG. 3, the surgeon disconnects the implanted device 232 from the screener cable 320, the latter of which are discarded, and continues with the surgery including the percutaneous placement and attachment of the vendor provided implantable pulse generator 242, FIG. 2, to the SCS paddle lead 232.

An exemplary mapping sequence is now described for the exemplary system embodiment of FIG. 3. As noted previously, and in advance of surgery, the contacts 234 of the implantable SCS Penta paddle lead 232 are initially drawn on a piece of paper or otherwise with their numbered designations. As previously noted and with reference to FIGS. 4(b) and 4(c), the Penta implantable SCS paddle electrode 232 includes 5 columns, each column having four (4) contacts for a total of (20) twenty electrical contacts. According to this specific embodiment and in terms of designation, as shown in FIG. 4(c), the first column of the SCS paddle lead 232 is sequenced reading down with the following contact designations: 1, 1, 2, 2. The second column is sequenced with the following contact designations: 3, 4, 5, 6. The third column of the herein described SCS paddle lead 232 is sequenced with the following contact designations: 7, 8, 9, 10, the fourth column is sequenced: 11, 12, 13, 14 and the fifth column of the SCS paddle lead 232 is sequenced with the following contact designations: 15, 15, 16, 16.

According to this mapping approach, the electrical contacts 234 of the SCS paddle 232 are then selected and assigned to an anode/cathode: e.g., 3/4, 5/6, 7/8, 9/10, 11/12, 13/14, etc. in order to stimulate the various contacts and for obtaining recording (cortical) signals and peripheral recordings from the patient. The contacts 234 are then made to the designated neurophysiological monitoring apparatus/equipment and according to this specific technique, peripheral electrodes are also positioned at the wrist and back of the knee with the electrode outputs being connected to the IONM device. Recordings are obtained from the popliteal fossa or the ulnar nerve at the wrist in which the recording signals are transmitted through the connecting apparatus to the remotely located IONM for evaluation.

In accordance with another example, a Boston Scientific 2×8 electrode similar to that shown in FIGS. 2, 4(d), and 4(e), is implanted surgically within the spinal column of a patient. With this specific paddle electrode 232A and as shown in FIG. 9, the electrical contacts 234A are numbered 1-8 in each of the two columns.

Figure 8:
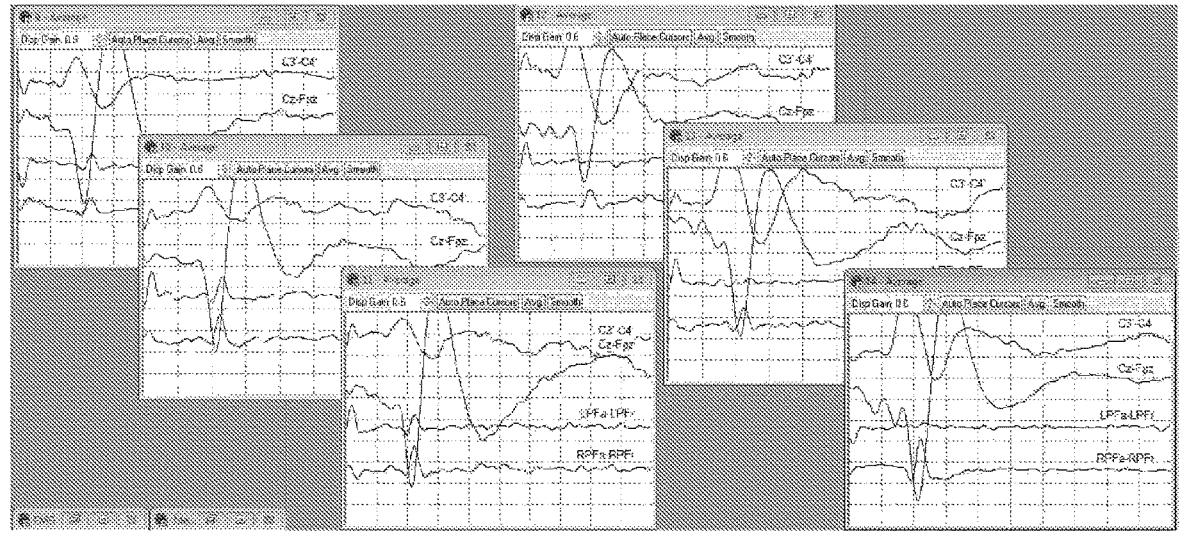
FIGS. 8(a) and 8(b) depict exemplary outputs of recorded signals obtained via a connected neurophysiologic monitoring device and in accordance with various aspects of the present invention.
Figure 8:
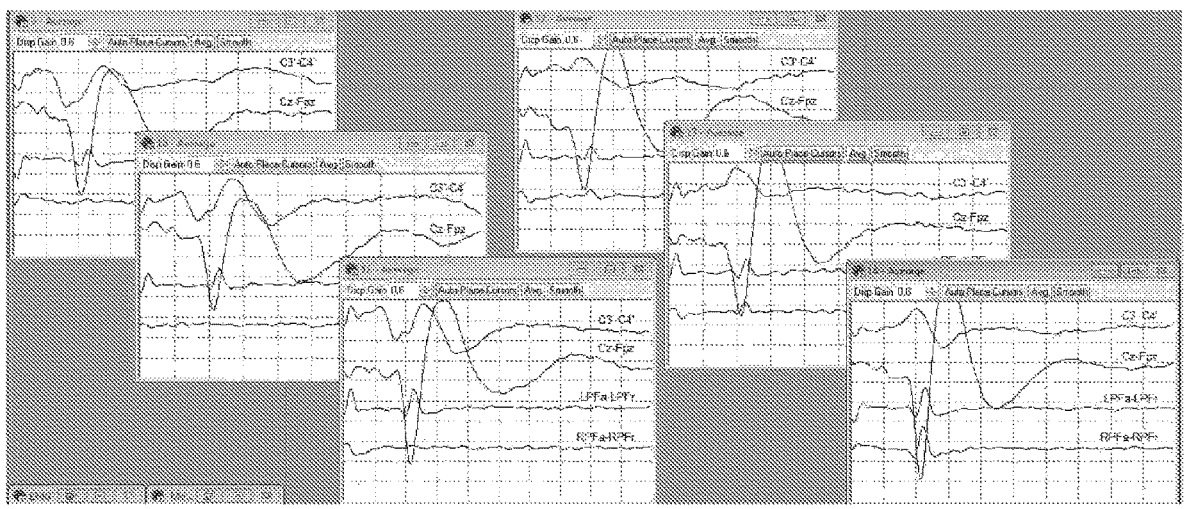
Figure 9:
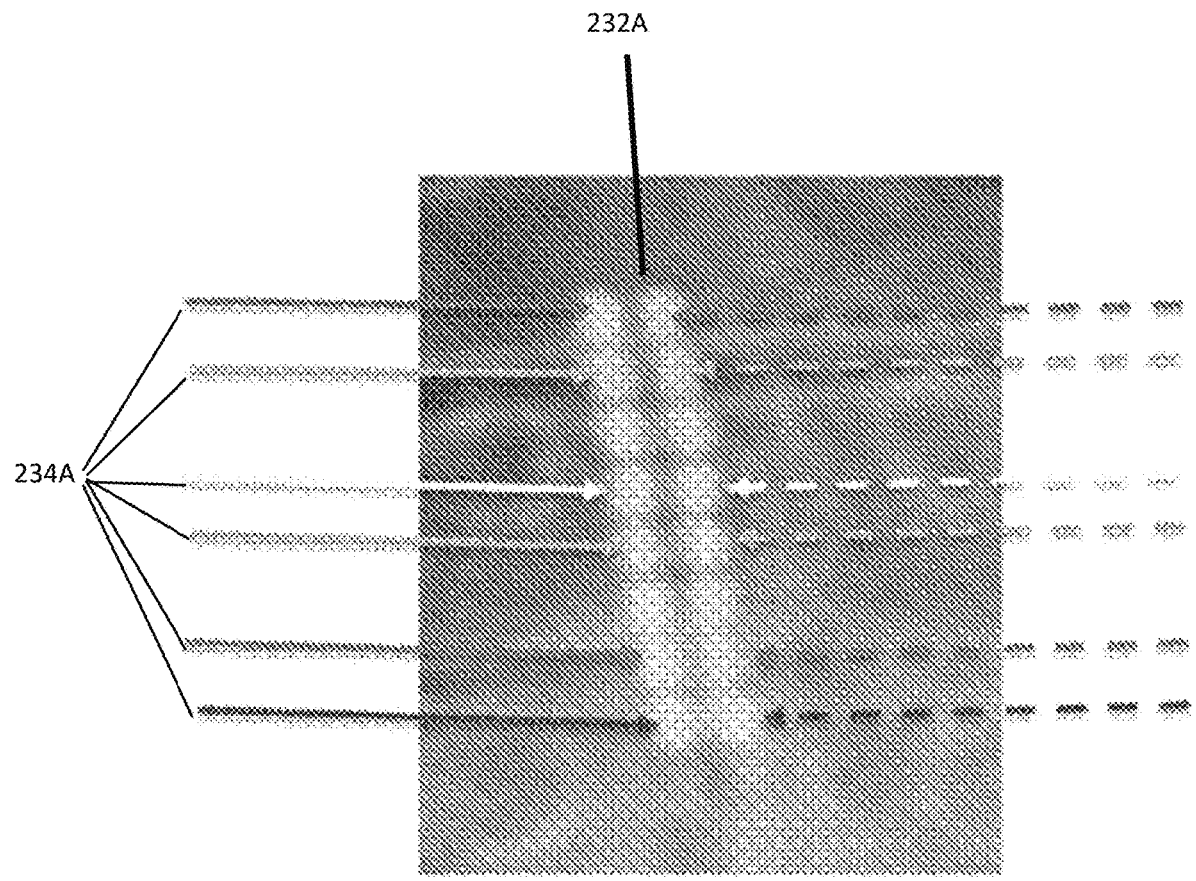
FIG. 9 is a partial view of an exemplary neuromodulating device, specifically the implantable electrode stimulation device where the device is surgically implanted within the patient.

As shown in FIG. 9, the electrical contacts 234A numbered 1, 2, 4, 5, 7, 8 were selected for stimulation bilaterally. Cathodes (−) consisted of contacts indicated by the orange, green, and purple arrows (both dashed and solid). Anodes (+) represent the remaining depicted arrows. Accordingly, the stimulation anode/cathode pairs according to this example were red/orange, yellow/green, and blue/purple (both dashed and solid). Following connection to the neurophysiological equipment using the connector apparatus as discussed above and when the electrical contacts, which are designated by the solid red and orange arrow were stimulated, these contacts produced the signals that can be seen in the upper left most window of FIG. 8(a) (designated "9" in the upper left portion of the depicted window). The recording montages in window 9 are C3-C4 and Cz-Fpz and represent the top two lines. The lower two lines in this window are recorded from the posterior aspect of the knee (popiteal fossa) of the left and right leg. These montage designations can be seen in window 11 as LPFa-LPFr for the left leg and RPFa-RPFr for the right leg. The lowermost line represents the right leg response. As can be seen in window 9, the lower two lines have two equal sized deflections that indicate a midline placement of the electrical contacts designated by the red and orange solid arrows. In the lower right window of FIG. 2 (which are labeled as "14" in the upper left corner of that window), there is only one upward deflection in the lower two lines. This upward deflection is occurring only in the right leg, thereby indicating that the electrical contacts designated by the blue and purple dashed arrows are positioned to the right of the anatomical midline.

Antidromic peripheral/orthodromic cortical recordings are presented in FIG. 8(a), demonstrating right biased placement of the paddle electrode. Each of the windows 9, 10, 11 on the left were recorded from stimulation to electrical contacts on the left side of the implanted electrode. Window 9 depicts the result of stimulation to the contacts as designated previously by the red and orange solid arrows of the depicted electrode, window 10 depicts the recording signals resulting from stimulation to the contacts designated by the yellow and green solid arrow contacts. Window 11 depicts the recording signals in response to stimulating the blue and purple solid arrow electrical contacts of the implanted electrode. Windows 12, 13, 14 on the right were recorded from stimulation to the right of the implanted electrode. More specifically, window 12 depicts the response to stimulation of the electrical contacts designated by the red and orange dashed arrows, while window 13 depicts the response to stimulation of the electrical contacts designated by the yellow and green solid arrow contacts and window 14 depicts the recording signals in response to stimulating the blue and purple solid arrow electrical contacts of the implanted electrode.

In the left three windows (windows 9, 10, 11), there is an upward deflection in both of the lower two lines that indicate that the electrical contacts on the left side of the implanted electrode are close to the anatomical midline of the spinal cord. The right three windows (windows 12, 13, 14) only demonstrate a deflection in the lower most lines, indicating that the contacts on the right side of the electrode are to the right of the anatomical midline.

FIG. 8(b) depicts the opposite result (left biased placement) in which the anatomical midline is recorded in the three windows on the right side of the figure and left response are recorded in the three remaining windows.

More specifically, the windows designated windows 9, 10, 11 on the left were recorded from stimulation to contacts on the left side of the implanted electrode. Windows 12, 13, 14 on the right of this figure were recorded from stimulation to the right of the electrode. Cortical responses, which are represented by the aforementioned montages C3-C4 and Cz-FPz are represented in the top two lines of each window. Note that in FIG. 8(b), the three windows on the left both deflect upward and the three windows on the right have opposing deflections. This range of polarity of the deflection in the C3-C4 montage is caused by different sides of the brain responding to stimulation from the implanted electrode. Due to this phenomena, called paradoxical laterization in this case, the response of the brain to stimulation of the spinal cord can be used to localize the implanted electrode.

According to this mapping technique and during stimulation, the surgical team is directed to feel and watch for muscular movement from the patient at directed areas. Stimulation should be increased until an averaged signal can be resolved by the IONM. Individuals who do not have peripheral neuropathy should display a nerve action potential in the popliteal fossa recordings. According to this embodiment and if the nerve action potential cannot be elicited from the popliteal fossa, increased stimulation will produce a compound action potential (CMAP) in the recordings. Cortical response and movement reported by the surgical team can also be used to verify electrode positioning.

As noted, other mapping sequences can also be employed using the herein described system and one or more of the mapping techniques can be used contemporaneously using the herein described connector apparatus. For example, mapping sequences employing the so-called "collision approach", as well as those that employ traditional EMG can be used. Literally any known mapping technique can be utilized according to the present invention, including but not limited to the following: Dorsal Root Ganglion stimulation (DRG-S), paresthesia-free (SCS) paradigms, Burst SCS (B-SCS), High-Frequency (HF-SCS) and Evoked Compound Action Potential SCS (ECAP-SCS), among others.

In general, the numbered DIN connectors of the connecting apparatus 400 according to the present invention can be connected to a wide variety of neurophysiological devices, including but not limited to neuromonitoring equipment, EEG equipment, and single unit recording/stimulation devices. Because the numbering of the electrode connector pins on the connecting apparatus is known, any contact on the implanted electrode can individually be selected as either a recording or a stimulating contact. This advantageously permits a wide variety of neurophysiological tests to be carried out, as needed, in order to map the spinal cord. Present day methodology is based on recording from muscle groups on either side of the appendages of the patient and verifications if responses are present. It is also possible to stimulate the extremities and record from the implanted electrode. Stimulation through the electrode and recording nearfield nerve action potentials (NAP) from the appendages, as well as resolution of cortical signals is also possible.

PARTS LIST FOR FIGS. 1-8(b)

100 system
120 neurostimulation device
130 neurophysiological device/equipment
150 connecting apparatus
200 neurostimulation or neuromodulation device
232 232A surgically implantable spinal cord stimulation (SCS) paddle lead
234 234A electrical contacts
235 paddle electrode
238 wire leads
242 implantable pulse generator
300 system
320 screener cable
324 distal portion
328 connector port
400 connecting apparatus
402 insulated cable
404 connector port
407 center pinned socket
409 outer enclosure
412 hub
416 plurality of electrode pin (DIN) connectors
500 flow chart
502 step
506 step
510 step
514 step
518 step
522 step It will be readily apparent that other modifications and revisions are possible within the intended ambits of the present invention. For example, the wired connections described in accordance with the exemplary embodiments can alternatively be wireless. Other suitable variations and modifications will be understood, as will be gleaned from the following claims.

What is claimed is:

1. A method of neurostimulation, comprising connecting a surgically implanted neurostimulation device to a neurophysiologic monitoring device for mapping of electrodes of the neurostimulation device, the method comprising:
- connecting the surgically implanted neurostimulation device to a connection apparatus;
- connecting the connecting apparatus to the neurophysiological monitoring device; and
- transmitting at least one stimulation signal using the neurophysiological monitoring device via the connecting apparatus to the neurostimulation device and obtaining at least one recording signal at the neurophysiological monitoring device from the neurostimulation device via the connecting apparatus based on the at least one stimulation signal;

wherein the connecting apparatus comprises a connector port for connection to the neurostimulation device and a plurality of electrode pin leads for connection to the neurophysiological monitoring device, and wherein each pin lead in the plurality of electrode pin leads is independently configured to transmit either a stimulation signal or a recording signal.

2. The method according to claim 1, in which the neurophysiological monitoring device is an IONM device.

3. The method according to claim 1, in which the neurostimulation device is a spinal cord stimulation device (SCS).

4. The method according to claim 1, in which the neurostimulation device is wirelessly connected to the connecting apparatus.

5. The method according to claim 1, in which the neurostimulation is one of the groups consisting of Spinal Cord Stimulation (SCS), Deep Brain Stimulation (DBS), Peripheral Nerve Stimulation (PNS), and Functional Electrical Stimulation (FES).

6. The method of claim 5, in which the neurostimulation is SCS selected from the group consisting of Dorsal Root Ganglion stimulation (DRG-S), paresthesia-free SCS (SCS), Burst SCS (B-SCS), High-Frequency SCS (HF-SCS), and Evoked Compound Action Potential SCS (ECAP-SCS).

7. The method according to claim 1, in which the plurality of electrode pin leads comprises DIN pin connectors.

8. The method according to claim 1, in which mapping of the spinal cord is done by recording directly from nerve action potentials following stimulation.

* * * * *